United States Patent [19]
Garfield et al.

[11] Patent Number: 5,313,938
[45] Date of Patent: May 24, 1994

[54] VALVED RESUSCITATION PUMP HAVING SECRETION REMOVAL MEANS

[75] Inventors: Allan S. Garfield, 2 Lockerbie Court, East St. Kilda, Victoria 3183; Noam White, Balaclava; Max S. de Vriend, Caulfield; David J. Cook, E. St. Kilda, all of Australia

[73] Assignee: Allen Samuel Garfield, East St. Kilda, Australia

[21] Appl. No.: 944,929

[22] Filed: Sep. 15, 1992

Related U.S. Application Data

[63] Continuation-in-part of Ser. No. 302,693, filed as PCT/AU87/00170, Jun. 10, 1987, abandoned.

[30] Foreign Application Priority Data

Jun. 18, 1986 [AU] Australia ............................... PH6459

[51] Int. Cl.⁵ ............................ A62B 7/00; A62B 9/02
[52] U.S. Cl. ........................... 128/205.16; 128/205.13; 128/205.24
[58] Field of Search ....................... 128/200.24, 204.18, 128/205.13, 205.16, 205.19, 28, 30, 30.2, 205.24

[56] References Cited

U.S. PATENT DOCUMENTS

| 2,547 | 4/1842 | Welchman | 128/205.13 |
| 2,737,177 | 3/1956 | Anklin | 128/205.13 |
| 3,215,413 | 11/1965 | Mota . | |
| 3,323,521 | 6/1967 | Isk | 128/205.16 |
| 3,336,920 | 8/1967 | Thomas | 128/205.16 |
| 3,530,857 | 9/1970 | Miczka | 128/205.13 |
| 3,782,371 | 1/1974 | Derouineau | 128/28 |
| 3,882,860 | 5/1975 | Frimberger | 128/205.13 |
| 3,965,893 | 6/1976 | Ragailler | 128/28 |
| 4,297,999 | 11/1981 | Kitrell | 128/205.16 |
| 4,349,015 | 9/1982 | Alferness | 128/28 |
| 4,570,615 | 2/1986 | Barkalow | 128/28 |
| 4,934,360 | 6/1990 | Heilbron et al. | 128/205.16 |

FOREIGN PATENT DOCUMENTS

| 243720 | 1/1963 | Australia | 128/205.13 |
| 42999/72 | 12/1973 | Australia . | |
| 623708 | 2/1962 | Belgium | 128/205.13 |
| 54419 | 2/1938 | Denmark | 128/205.13 |
| 0048164 | 3/1982 | European Pat. Off. . | |
| 2413770 | 10/1975 | Fed. Rep. of Germany . | |
| 865326 | 5/1941 | France | 128/205.13 |
| 916021 | 11/1946 | France . | |
| 1209699 | 3/1960 | France | 128/205.13 |
| 1223630 | 6/1960 | France | 128/205.13 |
| 1337050 | 7/1963 | France . | |
| 467733 | 6/1937 | United Kingdom | 128/205.13 |
| 8707844 | 12/1987 | World Int. Prop. O. | 128/205.13 |

Primary Examiner—David A. Wiecking
Assistant Examiner—Kimberly L. Asher
Attorney, Agent, or Firm—Finnegan, Henderson, Farabow, Garrett & Dunner

[57] ABSTRACT

A cardiopulmonary resuscitating pump, comprising, a housing having a top wall (20), a bottom wall (21) and a side wall (22) in the form of a bellows which is capable of contracting and expanding under the application and release of an externally applied pressure to contract and expand the volume of a gas chamber (23) within the housing and having a gas inlet (48) through the bottom wall for drawing gas into the gas chamber and a gas outlet (43) through the bottom wall for discharging gas from the gas chamber to an associated oropharyngeal airway, whereby, in use a patient can be subjected to ventilation and external cardiac massage by appropriate operation of the pump whilst situated on the patient's chest. A waste chamber (29) is also provided attached to the bottom wall and communicating, via a waste inlet (52) through the bottom wall, with the associated oropharyngeal airway whereby to suck secretions from the patient whilst cardiac massage and ventilation is occurring and to expel secretions through a waste outlet (47) through the bottom wall. Biasing springs (24 and 33) are provided in both the gas and waste chamber to assist in expanding the volume of the chambers upon release of the externally applied pressure, and all inlets and outlets contain check valves (42, 46, 49 and 53) to prevent reverse flow therethrough.

15 Claims, 6 Drawing Sheets

VALVED RESUSCITATION PUMP HAVING SECRETION REMOVAL MEANS

TECHNICAL FIELD

This invention relates to resuscitators and in particular to cardiopulmonary resuscitation devices suitable for use primarily in a non-hospital setting. This application is a continuation-in-part to applicants' earlier U.S. application U.S. Ser. No. 07/302,693, filed as PCT/AU87/00170, Jun. 10, 1987, now abondoned, which applicants relied upon and incorporated herein by reference.

BACKGROUND ART

It has long been recognised that one of the most frequently encountered medical emergencies is loss of cardiorespiratory function necessitating resuscitation.

Basic cardiopulmonary resuscitation ('Basic CPR') refers to maintenance of essential life functions in situations of cardiorespiratory arrest, i.e. where spontaneous breathing is absent and no pulse is present due to inadequate cardiac output. In adults, this arrest is most often due to 'cardiac arrest' (e.g. myocardial infarction), whereas in children it is more often secondary to 'respiratory arrest' or hypoxia e.g. asphyxia.

Basic CPR is the accepted technique out of hospital where advanced life support systems are not available. Examples of situations where basic CPR is essential include drowning, trauma, drug overdose, and myocardial infarction.

It has been shown that Basic CPR, when performed adequately, will satisfy the physiological criterion of maintaining delivery of oxygen and nutrients to vital tissues, in order to preserve their cellular function.

Basic CPR can be performed by two techniques: (a) 'Old' CPR and (b) 'New' CPR, which will be described in more detail as follows:

(a) 'Old' CPR is well-established in the medical literature.

The basic technique where no specialised equipment is available is to clear the airways of solid or fluid matter, position the patient supine with neck extended and tongue brought forward, and then to apply positive pressure breathing at a rate of 10–15/min (e.g. mouth-to-mouth, or by mask), together with external cardiac compression at a rate of 80–100/min.

This ideally requires two trained operators. Although it can be performed by one trained operator, this is much less efficient due both to the technique itself and to the physical strain involved.

The basis for the technique is that the increase in intrathoracic pressure is transmitted to the heart; when performed properly, it has been shown to generate 15–25% of normal cardiac output. This results in predominantly 'forward' blood flow to the brain, as the valves in the great veins in the neck prevent reverse flow.

(b) 'New' CPR has been described only very recently. It follows the same basic theory as 'old' CPR, except that it recommends the simultaneous performance of both external cardiac compression and ventilation, resulting in a greatly enhanced forward blood flow and cardiac output, because of a greater increase in intrathoracic pressure that is transmitted in the heart. It is possible that coronary blood flow is increased and that myocardial perfusion is significantly improved.

CPR is known among the general (non-medical) community to varying degrees, and training courses are offered by various organizations. For example, in Seattle, U.S.A., a community program has resulted in training of a very high proportion of the community.

In order for a CPR method to be of use, it must be
a) Simple to understand and perform.
b) Effective in maintaining an adequate cardiac output and respiration.
c) Acceptable to the user.

The performance of mouth-to-mouth resuscitation is a particular problem. Lay persons with some training in first aid seem less likely to hesitate in an emergency to apply mouth-to-mouth ventilation (Safar, P., in "Critical Care, State of the Art" ed. W.C. Shoemaker and L.L. Thompson S1-S65 (1981)). However, it seems that hospital personnel are more reluctant, as in a recent study up to 30% of 70 subjects would at times make a judgement in the community setting prejudicial to a victim's survival (Lawrence, P.J. and N. Sivaneswaran, (1985): Med. J. Aust. 143 443–446). In particular, it is well-known that people are reluctant to administer mouth-to-mouth resuscitation to patients who have vomited, have purulent sputum or copious secretions, or who are known to be infected. In the study already cited, only 49 (70%) of the 70 subjects were prepared to perform mouth-to-mouth ventilation for a victim in the community setting. Five subjects (7%) stated that they would not be prepared to use this method while 16 (23%) would use it only selectively, according to such influences as age of the victim, the presence of vomitus, evidence of intravenous drug abuse, and state of hygiene.

The responses for resuscitation in the hospital setting were markedly different. Only 36 (51%) were prepared to use mouth-to-mouth resuscitation on a "clean" victim, and when vomitus or infected secretions were present only nine (13%) would be prepared to use mouth-to-mouth. Mouth-to-mask ventilation was accepted by 41 (59%) for all patients. The addition of a mouthpiece resulted in acceptance by all subjects for clean patients and by 67 (96%) for dirty patients. The addition of a bacterial filter resulted in 100% acceptance under all circumstances.

It is noteworthy, however, that this study was carried out before the recent very widespread publicity given to the acquired immune deficiency syndrome (AIDS). One may assume even less willingness would be found now, in spite of the absence of reported cases of AIDS transmission by this route. However, the AIDS-related HTLV-III virus is found in the saliva of both symptomatic and asymptomatic high-risk groups, (Groopman J.E., S.Z. Salahuddin, M.G. Sarngadharan et al. (1984): Science 226 447–449) and groups such as ambulance officers and police have refused to administer mouth-to-mouth resuscitation to those at risk of or suffering from AIDS.

Thus most potentially preventable deaths occurring in outside-the-hospital situations occur nowadays either because of ignorance of Basic CPR, inadequate knowledge of its applications, or aversion to its use because of the presence of secretions or vomitus, or the fear of transmissible disease, particularly AIDS.

The existing recommendations for emergency ventilation are for mouth-to-mouth ventilation or, if equipment is used, mouth-to-face mask ventilation, until the airway is assured by intubation (Standards and guidelines for cardiopulmonary resuscitation (CPR) and emergency cardiac care (ECC) JAMA—Volume 255, No. 21, Published Jun. 6, 1986 (pages 2905–2984). This seems not to have been accepted into current practice in many hospitals, where a variety of devices may confront a person attempting resuscitation. Pulmonary ventilation is frequently inadequate when these devices are used during CPR, unless special instruction is given, and one frequently used system, bag-valve-mask ventilation, had a 97% failure rate even after instruction (Lawrence and Sivaneswaran, op. cit).

Internationally accepted guidelines for CPR recommend that if equipment is to be used, then mouth-to-mask ventilation should be used until intubation is carried out, either endotracheally or with an oesophageal obturator airway (JAMA, op. cit.).

However, most mouth-to-mask methods require the operator to hold the mask to the patient's face using both hands. Consequently a second operator must be present if cardiac massage is to be applied, which gravely limits this method. More commonly such emergencies occur in situations where face masks are not available.

DISCLOSURE OF THE INVENTION

We have now devised a resuscitator which enables a single person to perform simultaneously the functions of
a) cardiac massage,
b) artificial respiration, and
c) suction of secretions from the airway, without placing the operator in contact with the patient's secretions until professional assistance arrives. The device is suitable for administering either air or an air-oxygen mixture of desired composition.

According to the present invention there is provided a cardiopulmonary resuscitating pump comprising a portable housing having a top wall with a gripping portion adapted to be hand held in use and a bottom wall with a side wall structure extending therebetween, the walls containing a gas chamber having a gas inlet and outlet and a waste chamber having a waste inlet and outlet; said gas outlet and waste inlet being adapted to be placed in fluid connection with an oropharyngeal airway; the bottom wall having a substantially planar undersurface adapted to, in use, rest on the chest of a patient; said side wall structure being capable of contracting and expanding upon the application and release of externally applied pressure manually applied to said top wall whereby, in use, as said side wall structure contracts gas is pumped from said gas chamber into the oropharyngeal airway via the gas outlet and waste is expelled from the waste chamber via the waste outlet and as said side wall structure expands, gas is drawn into the gas chamber via the gas inlet and secretions from the patient are sucked into the waste chamber from the oropharyngeal airway via the waste inlet, so that when the pump is on the chest of a patient and said side wall structure is contracted under the application of said externally applied pressure, application of further pressure will be transmitted to the patient via the bottom wall to effect simultaneous cardiac massage and ventilation.

BRIEF DESCRIPTION OF THE DRAWINGS

Two preferred embodiments of the invention will now be described by way of example only, with reference to the accompanying drawings, in which.

BEST MODES FOR CARRYING OUT THE INVENTION

Figure 1:
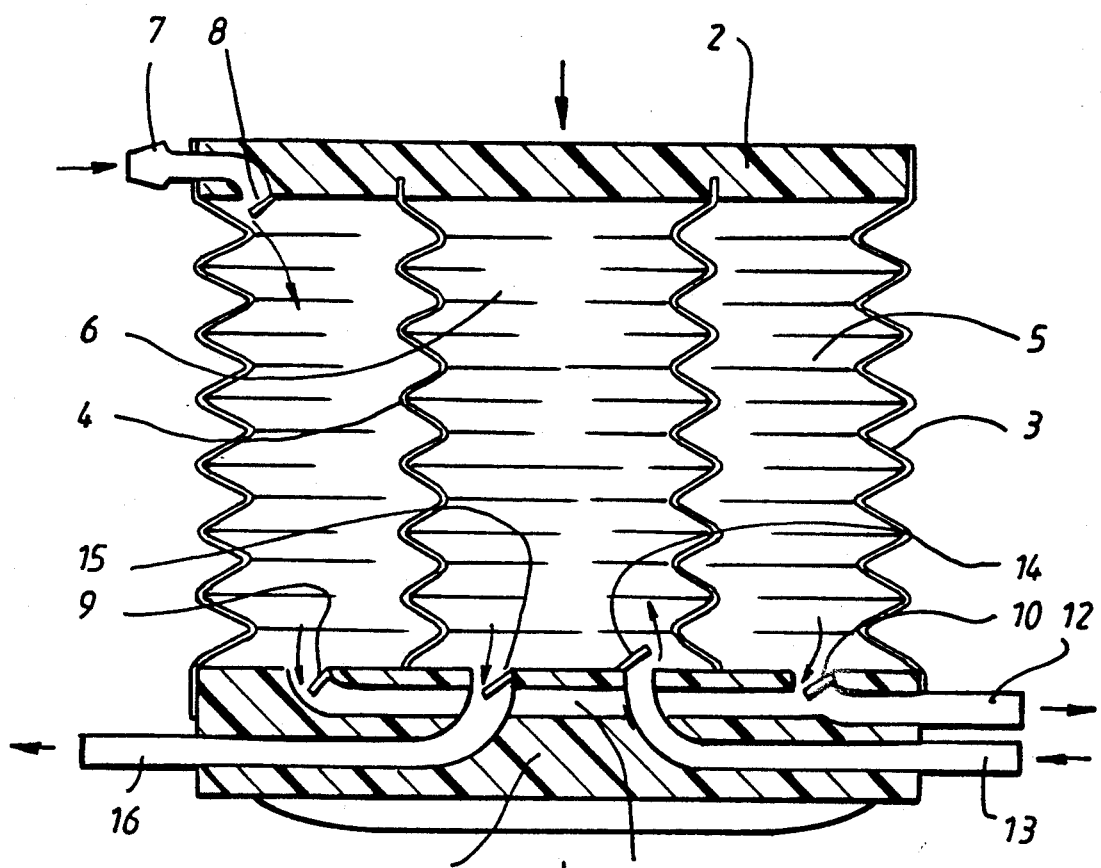
FIG. 1 is a vertical cross-section of a simplified version of the pump.

FIG. 1 shows a vertical cross-section through a simple version of the pump being one preferred embodiment of the invention, and which comprises a housing having a circular bottom wall 1 and a circular top wall 2, joined by a circumferentially extending cylindrical side wall 3 which, together with inner cylindrical side wall 4 defines an annular gas chamber 5. The side walls 3 and 4 are of a bellows construction such as to resiliently compress and expand as an axial force is applied to and released from the pump. Inner side wall 4 further defines a cylindrical waste chamber 6 which is centrally disposed within the pump. Gas (either air, oxygen, or an air-oxygen mixture) enters the gas chamber 5 via a gas inlet spigot 7 through the top wall 2 and one-way flap valve 8. When the operator applies hand pressure to the top face 2, as indicated by the arrow to axially compress the side walls 3 and 4, gas is expelled from gas chamber 5 through one-way flap valves 9 and 10 into gas outlet tubes 11 and 12 contained within and extending outwardly from the bottom wall 1. When the pressure is released, the resilient bellows construction of the side walls 3 and 4 causes chambers 5 and 6 to expand, thus causing further gas to enter at 7, and also causing any liquid in the mouth or pharynx of the patient to be extracted and sucked through a waste-venting tube 13 and a one-way valve 14 into the waste chamber 6. From there waste can leave via a one-way flap valve 15 via a waste outlet tube 16 to a waste reservoir (not shown). Expulsion of waste in this way is assisted by subsequent compression of the pump. The top face of the pump may carry means such as straps for steadying the hands of the operator.

Figure 7:
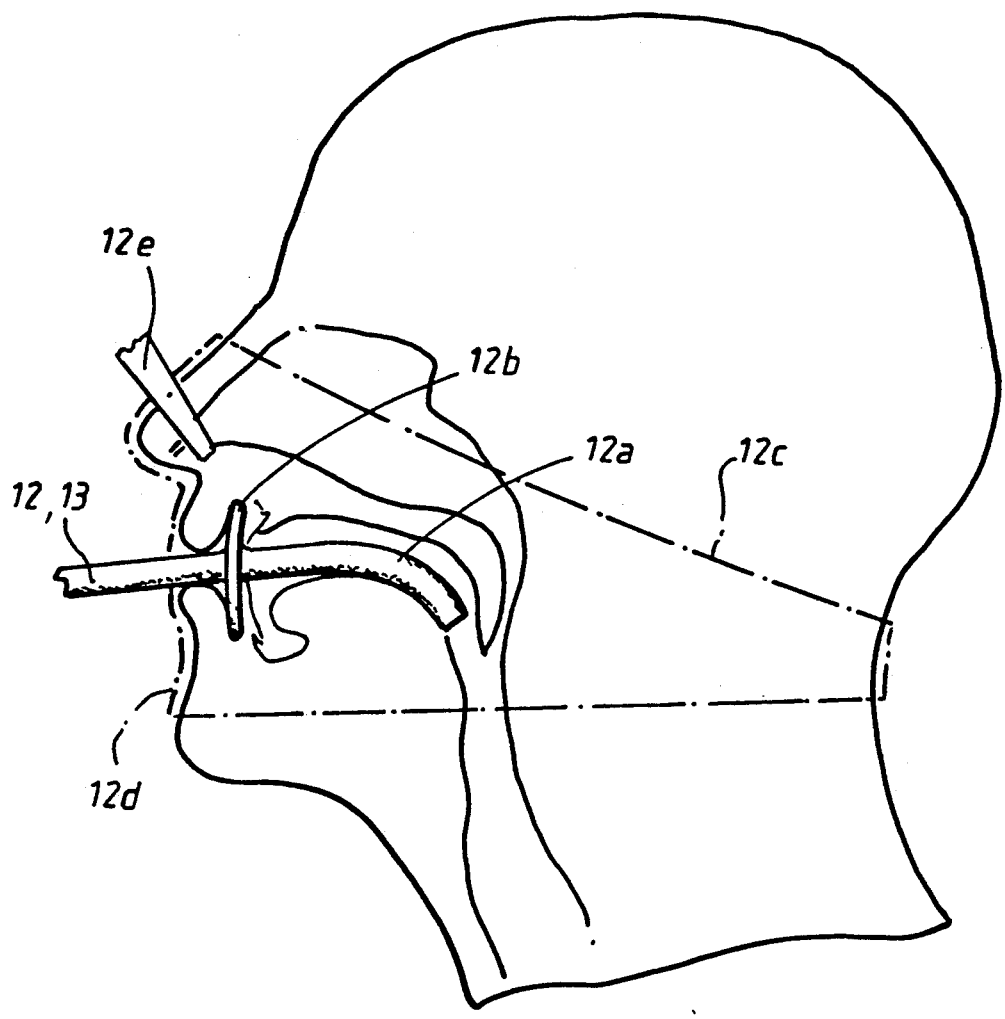
FIG. 7 is a side view of the oropharyngeal airway at the mouth of a patient.
Figure 8:
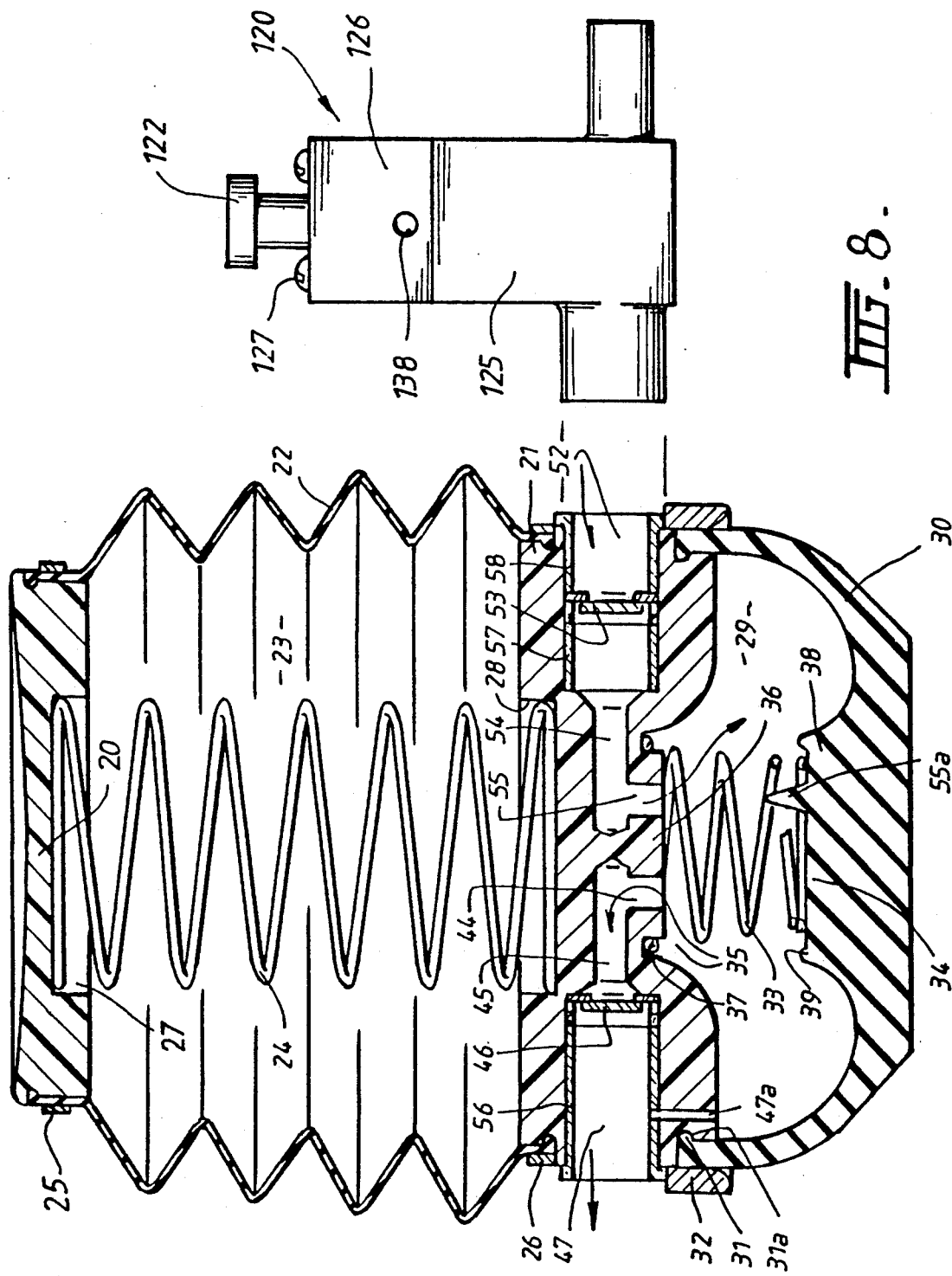
FIG. 8 is a view similar to FIG. 2 but showing a modification to the pump shown in FIG. 2.

With reference to FIG. 7, distal ends of tubes 12 and 13 form part of an oropharyngeal airway which has a pharyngeal piece 12a connected to a mouthpiece flange 12b and adapted to fit between the lips and gums of the patient. The pharyngeal piece houses the ends of the tubes 12 and 13 from the pump. The oropharyngeal airway has means for securing it to the patient's head such as, an elastic strap, or other detachable strap means 12c forming part of a mask 12d covering the patient's face at the mouth and nose regions, with a clamp 12e being provided to clamp the patient's nose and close the nasal passageways. As shown there is only one outlet from the pump to the oropharyngeal airway, but in an alternative arrangement there may be two outlets and two outlet tubes both terminating at the pharyngeal piece on either side of the waste-venting tube 13.

The pump may be made from any suitable sterilisable material, for example plastics, and such as to be of a lightweight, compact construction, and portable. It will preferably be produced as a ready-assembled unit, and is suitable for use as a disposable apparatus. There are no electrical components and no power source is required. As an alternative to the resilient bellows construction of the side walls 3 and 4, the side walls may be formed from telescoping wall members with an internal spring biasing the structure to an expanded condition, and compressible under pressure, and expandable when pressure is removed, to function in a similar manner to the bellows arrangement as described.

Figure 6:
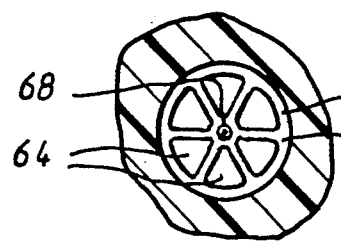
FIG. 6 is a cross-sectional view taken along line 6—6 of FIG. 5.
Figure 5:
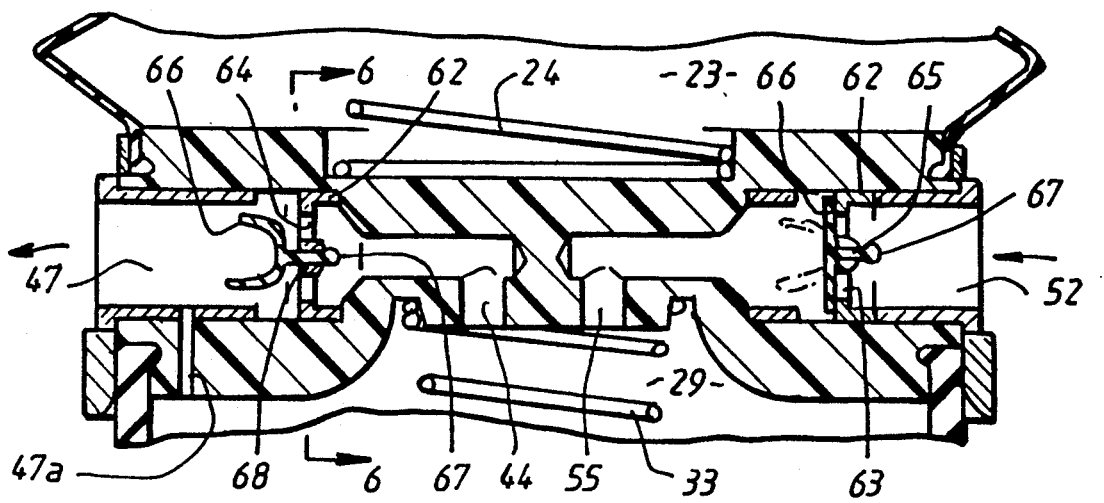
FIG. 5 is a cross-sectional view of the valve housing section of the pump of FIG. 2, but with an alternative form of valve for the various inlets and outlets.
Figure 2:
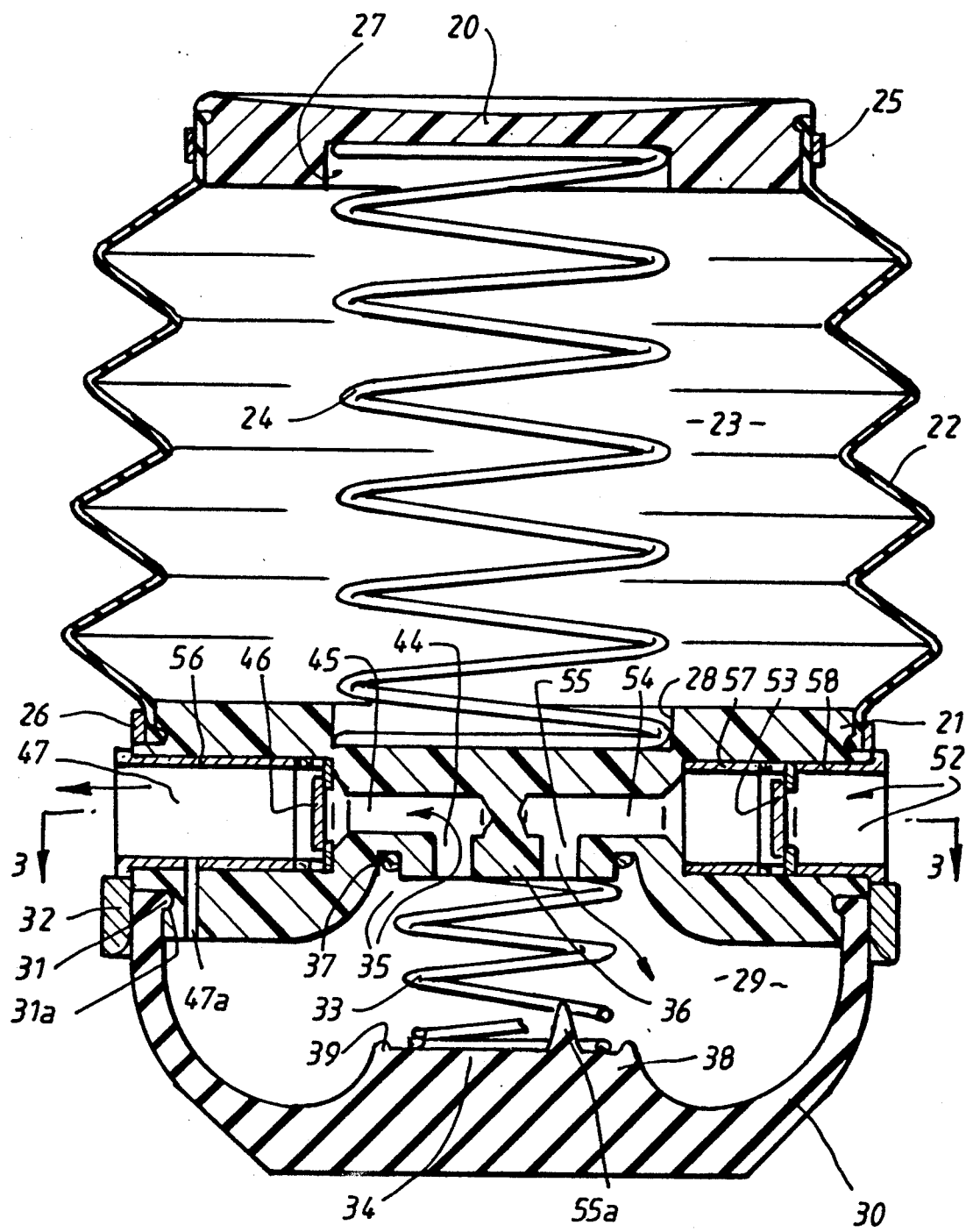
FIG. 2 is a vertical cross-section of a more sophisticated version of the pump.
Figure 3:
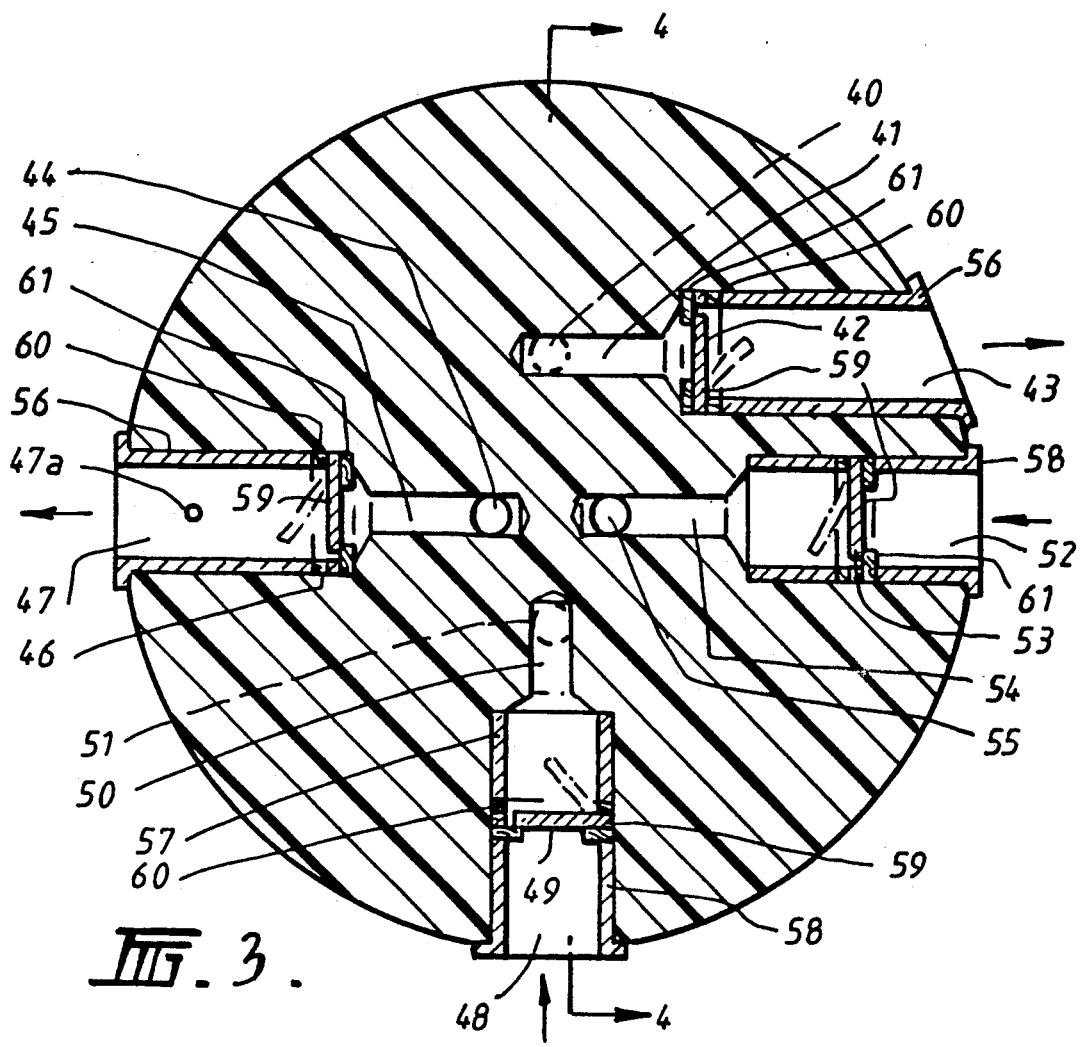
FIG. 3 is a cross-sectional view taken along line 3—3 of FIG. 2.
Figure 4:
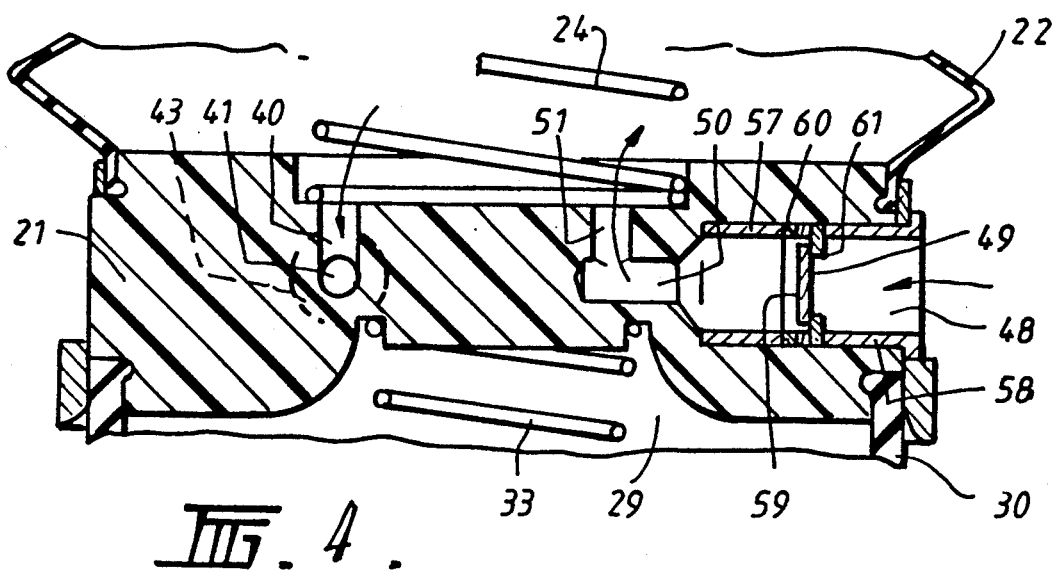
FIG. 4 is a cross-sectional view taken along line 4—4 of FIG. 3 and showing one form of valve arrangement for the various inlets and outlets from the pump.

In the more sophisticated embodiment of the invention with reference to FIGS. 2 to 4, and its alternative valve arrangement as shown in FIGS. 5 and 6, the pump comprises a circular top wall 20, and a circular bottom wall 21, joined by a circumferentially extending cylindrical side wall 22, clamped thereto by metal bands 25 and 26.

As with the embodiment of FIG. 1, the side wall 22 is of a bellows construction such as to resiliently compress and expand as an axial force is applied to and released from the pump. The space within and defined by the walls 20, 21 and 22 provides a gas chamber 23, and a compression spring 24 is positioned centrally within the gas chamber to bias the side wall 22 to its expanded or extended position as shown. The upper and lower ends of the biasing spring 24 are retained within circular recesses 27 and 28 provided on the underside of the top wall 20 and at the upper side of the bottom wall 21, respectively.

The underside of the bottom wall 21 carries a dome-shaped or cup-shaped waste housing 30 formed from semi-resilient material, and defining between itself and the bottom wall a waste chamber 29. The waste housing 30 is attached to the bottom wall 21 by means of a circumferentially extending, inwardly directed lip 31 on its upper edge engaged within a circumferentially extending groove 31a on the periphery of the bottom wall, with a clamping band 32 being additionally applied to consolidate the connection. A further compression spring 33, having a lesser spring force than the biasing spring 24 in the gas chamber, is positioned centrally with the waste chamber 29 between the bottom wall 21 and the opposing end wall 34 of the waste housing 30. As shown, the bottom side of the bottom wall 21 has a central depression 35 formed therein defining, with a central boss 36, a groove 37 for receiving the end of the spring 33, whilst the inner surface of the opposing end wall 34 of the waste housing has a central boss 38 formed thereon, with a circumferentially extending upstanding flange 39 within which the other end of the spring 33 is retained.

As axial pressure is applied to the pump, the semi-resilient nature of the wall of the waste housing allows it to deform to contract the space within the waste chamber 39, whilst upon release of the axial pressure the spring 33 returns the housing to its undeformed condition and the space within the waste chamber 29 expands to its original volume.

With reference to FIGS. 2 to 4, when an operator applies axial hand pressure to the top wall 20 of the pump, the side wall 22 is compressed against the biasing force of the spring 24 within the gas chamber 23 and gas within that chamber is expelled therefrom through a gas outlet port 40 in the bottom wall 21 and into a radial gas transfer port 41, past a gas outlet check valve 42 to a gas outlet passage 43 and then onto a gas outlet tube leading to the oropharyngeal airway as described for the embodiment of FIG. 1. The axial pressure on the pump contracts the space within the waste chamber 29 to expel waste material previously sucked from the patient and accumulated within the waste chamber, but as the spring force for spring 33 is less than that for spring 24 the waste chamber 29 contracts before the gas chamber 23. The waste material passes out through a waste outlet port 44 in the bottom wall 21 and into a radially waste transfer passage 45, and then past a waste outlet check valve 46 to a waste outlet passage 47 and then onto a suitable receptacle for disposal.

Upon release of the axial pressure applied by the operator, the biasing springs 24 and 33 in the gas and waste chambers 23 and 29 respectively, expand the chambers to their maximum volumes, and replacement gas is drawn from a gas supply or the surrounding atmosphere into the gas chamber 23 through a gas inlet passage 48 in the bottom wall 21, past a gas inlet check valve 49 into a gas inlet transfer passage 50 and onto a gas inlet port 51 to enter the gas chamber 23. Simultaneously, waste material from within the mouth or pharynx of the patient is drawn through a waste venting tube from the oropharyngeal airway, to a waste inlet passage 52 in the bottom wall 21, which in turn communicates, via a waste inlet check valve 53, with a radial waste transfer port 54 and waste inlet port 55 leading to the waste chamber 29. The continuous application and release of axial pressure on the pump by the operator as discussed above causes repeated ventilation and waste extraction operations through the oropharyngeal airway, whilst when axial pressure is maintained, repeated application and release of increased pressure through the pump body, whilst the pump is situated on the chest of the patient, applies external cardiac message or compressions.

There is a tendency at the pharyngeal piece within the patient for gas to flow from the gas tubes directly into the waste-venting tube and back to the waste chamber, rather than into the respiratory system of the patient, and in order to prevent such from happening in the embodiment of FIG. 2, a conical valve member 55a is provided within the waste chamber 29 on the inside wall of the waste housing 30 aligned with the waste inlet port 44, such that, when the waste housing is collapsed the valve member closes the port 55 and thus any bypassing of the gas back through to the waste chamber 29 is resisted ensuring that the gas therefore flows into the respiratory system of the patient.

Also, as shown in FIG. 2, a bleed port 47a is provided between the waste chamber 29 and the waste outlet passage 47, whereby, when waste is expelled through the waste outlet, and the waste outlet check valve 46 closes, air within the outlet can re-enter the waste chamber through the bleed port 47a to in effect release the vacuum, that is, raise the pressure within the waste chamber to match the outside pressure within the outlet 47.

In the embodiment of FIG. 2 to 4, the check valves 42, 46, 49 and 53 are in the form of simple flap valves positioned within the respective passages and held in place at the inner ends of the gas and waste outlet passages by elongate sleeves 56, whilst in the case of the gas and waste inlet passages, the check valves are captured between inner sleeves 57, at the inner end of the respective inlet passages, and outer sleeves 58, whereby the check valves are positioned midway along the length of those passages to ensure sufficient space for the flaps of the check valves to swing to an open position. Each check valve comprises a thin disc of semi-rigid material, with a circular slit cut around the disc radially inwardly of its circumference except for a small portion which forms a hinge attached to the separated inner part of the disc which in turn forms a flap 59. The disc is captured between a pair of washers 60 and 61, one having an internal diameter larger than that of the flap 59 (washer 60) and the other (61) having an internal diameter less than that of the flap 59. The first of the walls is positioned on the downstream side of the flap to allow the flap to swing open, whilst the other washer is on the upstream side to prevent the flap from opening in that direction under the influence of a reversed flow or pressure.

In the alternative embodiment of FIGS. 5 and 6, the check valves consist of "curl-type" valves comprises a housing having a cylindrical wall 62, one end of which is closed by a spoke-shaped wall 63 having a plurality of segmental apertures 64 formed therethrough. The central hub portion of the wall 63 has an aperture 68 therethrough which receives a stem 65 of a valve closure disc 66. A bulb 67 is formed on the free end of the stem 65 which, in the assembly of the check valve deforms when pushed through the aperture 68, but will prevent disengagement from within the aperture under normal operating pressures. Under downstream flow conditions, pressure on the disc 66 through the aperture 64 forces the disc away from the wall 63, whilst its outer periphery curls in the direction of fluid flow to provide a flow path around the disc, whilst under reversed flow or pressure conditions, the disc is pushed flat against the wall 63 to close the apertures 64. As with the embodiment of FIG. 1, the pump may be provided with two outlets from the gas chamber, for example an additional identical gas outlet and valve arrangement on the opposite side of the waste inlet, and each communicating with its own outlet tube leading to the pharyngeal piece and terminating on either side of the distal part of the waste-venting tube.

In order to provide adequate ventilation for an adult (0.8 L tidal volume; Lawrence and Sivaneswaran, op. cit.), the gas chamber should have a volume of approximately 1 L to achieve the required volume. The waste chamber should have a volume of approximately 0.2 L. Smaller sizes suitable for use with child patients are also within the scope of the invention.

OPERATION OF THE RESUSCITATOR FOR AN AVERAGE ADULT

A simplified, well-illustrated set of instructions will accompany each device, and the following steps will be detailed.

Step 1
a) Quickly confirm that the patient has no pulse, and is not breathing.
b) Lie patient on back on firm surface, preferably with the neck extended backwards.
c) Quickly loosen or remove all clothing around the neck and chest.
d) Where possible, clear the patient's mouth and airway of all visible fluid or particulate matter, and remove dentures.

Step 2
a) Insert the oropharyngeal airway over and behind the patient's tongue all the way back, until the flange lies against the patient's teeth or gums.
b) Tightly secure the attached band around the patient's head to keep the airway firmly in place.
c) Ensure that there are no kinks in the connecting tubing.

Step 3
a) If oxygen is available, connect the oxygen lead to the gas spigot at the top of the pump, and turn the flow on (approximately 2 to 4 L/min).
b) The operator should be kneeling by the side of the patient, leaning over the patient's chest and device as shown.
c) Place the bottom of the pump on to the lower part of the sternum and hold the unit upright but firmly in place with the flat of each hand on top of the other, parallel to the patient's chest and crossed at 90° to each other. The fingers of each hand should be firmly gripped to the rim of the top of the unit and away from the 'Air/oxygen' inlet.
d) Always maintain the pump vertically upright.

Step 4: CPR will thus begin in 7 - second cycles i.e.
a) 1-second 'ventilation', then
b) 10×$\frac{1}{2}$-second 'cardiac compressions' then
c) 1-second 'suction'.

(1) In a single action, firm compression straight downwards by the movement of both hands, will collapse the unit and inflate the patient's chest, i.e. a 1-second action 'ventilation'. Maintain this downward pressure to keep the unit deflated.

(2) Apply further pressure to press the sternum downwards approximately 4–5 cm, then release to allow the sternum to rise whilst still keeping the pump deflated. This 'cardiac compression' should take $\frac{1}{2}$ second.

(3) Repeat step (2) a total of 10 times, each of $\frac{1}{2}$-second duration.

(4) Release pressure and allow the unit to re-expand over 1 second i.e. 'suction'. (Reduced pressure below an atmosphere pressure in the pump will allow air or $O_2$ to enter the gas chamber, whilst secretions or vomitus can enter separately into the waste chamber).

(5) Repeat step (1).

From now on, this manoeuvre which inflates the patient's lungs will also empty the waste chamber of its contents through a conduit, and away from both patient and operator.

(6) Repeat steps (2) to (5), and so on.

Thus, a periodic sequence of manual compressions will co-ordinate a 'ventilation', then maintain an inflated chest whilst performing 10 serial 'cardiac compressions', in accordance with the current theory of 'New' CPR, which is now an accepted practice.

ADVANTAGES AND APPLICATIONS

Previously there has been no device of which we are aware that is capable of performing the essentials of manually performed Basic CPR, in situations where no specialized equipment is accessible which has the features of:

Providing a combination of ventilation, cardiac compression, and suctioning and the additional preferred feature of removal of airways matter.

The resuscitator according to the present invention has the advantages of:
1. Applying the principles of 'New'CPR i.e. simultaneous maintenance of chest inflation and external cardiac compression (with the added advantage of regular automatic suctioning), to enhance cardiac output.
2. Providing a correctly positioned oropharyngeal airway that is firmly held in place.
3. Enabling a single operator to perform all functions.
4. Avoiding contact with secretions or vomitus, and hence the risk of transmissible diseases.
5. Is suitable to be provided as a ready-to-use unit, thus avoiding delay in application of resuscitation.
6. Being lightweight, portable, compact, and without electrical components.
7. Being adaptable for single use, disposable application.
8. Being suitable for lay and inexperienced persons, by providing the simplified, well-illustrated instructions.

Minimal training, however, would be ideal, to maximise its useful application.

The resuscitator according to the invention is suitable for use in a wide variety of locations where an emergency can arise, including workplaces, aircraft, restaurants, schools, sporting clubs, swimming pools and beaches. It is also suitable for use by emergency services such as ambulance, fire brigade and police, and life-saving clubs.

ADDITIONAL MATERIAL

In the introduction of the specification under the heading "Background Art", there is discussion of both the old and new CPR techniques. The new CPR technique concerns a simultaneous performance of both external cardiac compression and ventilation. It is generally considered that the combination of both compression and ventilation results in a greatly enhanced forward blood flow and cardiac output because of the greater increase in intrathoracic pressure that is transmitted to the heart. There is a division of opinion in the medical profession concerning the effectiveness of new CPR. There is a school of thought that takes the view that pressurising the lungs at the same time as compressing the chest can cause blocking of certain arteries thus negating the very purpose of the technique. Consequently, the inventors of the cardiopulmonary resuscitation device that is the subject of this application have designed the device so that it can be used both in the old and new CPR techniques. The disclosure with reference to FIGS. 1 to 7 effectively relates to a device that is specifically designed for use with the new CPR technique. Thus, the devices of both embodiments initially pump air into the lungs, seal off air escape and allow application of cardiac massage and then draw out air and secretions via the waste chamber. It should be noted that during the cardiac massage, there is no possibility of air escaping from the patient. Thus, the cardiac massage takes place with the lungs full of air.

In the embodiment shown in FIGS. 8 to 11, there is an illustration of a device that is substantially the same as the device that is illustrated in FIG. 2. However, a pressure release valve 120 is coupled adjacent the waste inlet 52. As the top wall 20 is depressed against the spring 24 compressing the bellows 22, air in the gas chamber is expelled through the air outlet and oropharungeal airway 12,13 into the patient. As the top plate 20 descends towards the base of the air chamber, the pressure release valve 120 is triggered by contact of a striker arm 121 that extends from the top plate 20 against a plunger 122 of the release valve 120 allowing the air that is contained in the lungs of the patient to be expelled via the oropharyngeal airway 12,13 to expel to atmosphere through the pressure release valve 120. Cardiac massage is then applied with the top plate 20 pressed down against the interface. When cardiac massage is complete, the top plate 20 is pulled upwardly and the suction chamber takes over. The pressure release valve 120 becomes closed again and the check valve 53 on the waste inlet 52 is open allowing gas and secretions to be drawn from the lungs of the patient in the same manner as described in the earlier embodiment.

Figure 9:
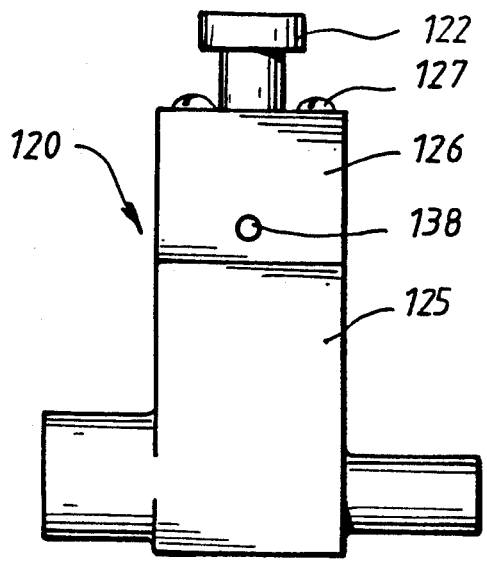
FIG. 9 is a side on view of a pressure release valve shown in FIG. 8.
Figure 11:
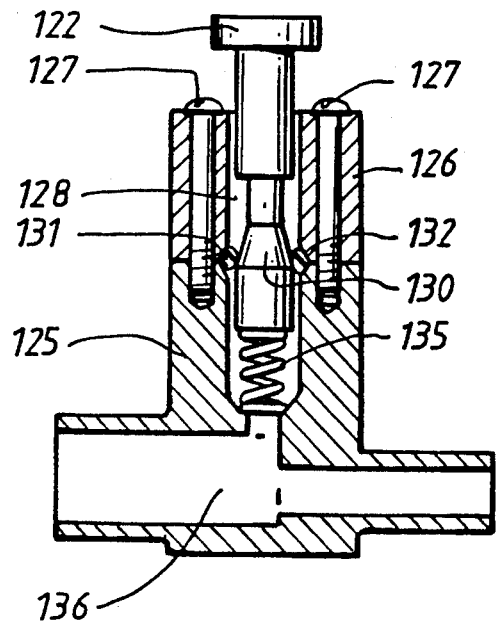
FIG. 11 is a cross-sectional view of the pressure release valve.
Figure 10:
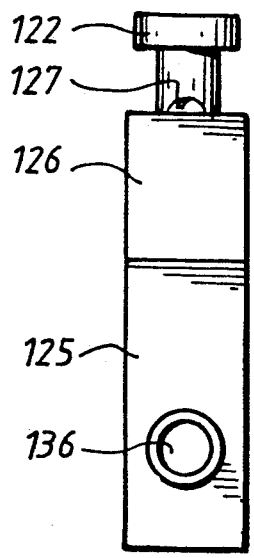
FIG. 10 is an end-on view of the pressure release valve.

Details of the pressure release valve 120 are shown with reference to FIGS. 9 to 11. The pressure release valve 120 comprises a housing in two parts 125 and 126, the top part 126 is secured to the lower part 125 by screws 127. Both parts define a throughway 128 into which is located the plunger 122. The plunger 122 has a frusto-conical valve seat 130 that is arranged to seal against an O-ring 131 positioned in an annular groove 132 in the wall of the throughway. The plunger 122 is mounted for axial displacement in the throughway about a coil spring 135. The throughway 128 that houses the plunger 122 is in fluid communication with an air duct 136 that extends mutually perpendicularly to the throughway 128. When the valve is in the closed position shown in FIG. 11, air and secretions from the lungs of the patient simply flow through the air duct 136 to the waste inlet 52 of the device. The valve is sealed by contact of the frusto conical valve seat 130 against the O-ring 131. The valve is opened by depression of the plunger 122 by the striker arm 121 on the top plate 20 of the resuscitating pump. Downward movement of the plunger 122 moves the frusto conical seat 130 away from the O-ring 131 and allows air that would be under pressure in the lungs of the patient to escape through the air duct 136 via a bleed hole 138 positioned in the wall of the upper part 126 of the valve. Once the top plate 20 returns the coil spring 135 urges the plunger 122 back to the sealed position of FIG. 11.

It is understood that the pressure release valve 120 shown in FIGS. 9 to 11 and its association with the resuscitating pump is only one means of effecting release of air pressure within the lungs of the patient. It is understood that many other types of valve could be incorporated within the broad scope of this invention and the valves could be housed within the pump assembly. It is further understood that a similar pressure release valve could be incorporated with the assembly shown in FIG. 1.

The pressure release valve 120 allows escape of the air pressure within the lungs of the patient prior to the cardiac massage but still allows the device to operate to suck waste air and secretions from the lungs of the patient. In this manner, the device can be used with the pressure release valve to perform old CPR or without the pressure release valve to perform new CPR. Consequently, the user of the device can by a simple change of the circuitry effect both CPR techniques in a simple expedient and sole operator mode.

Figure 12:
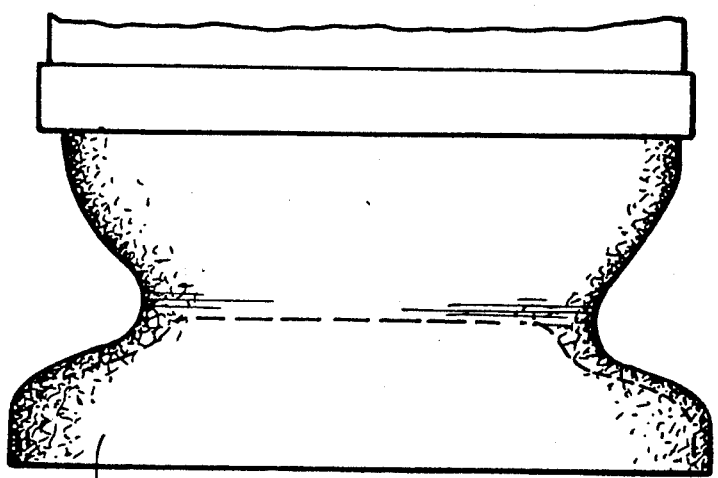
FIG. 12 is a side on view of the pump of FIGS. 2 or 8 with bellows on the base of the pump.

In a further embodiment shown in FIG. 12, a rubber or plastics bellows assembly 150 is formed on the base of the resuscitating pump. The bellows can be placed under pressure on the chest of the patient to act as a suction cup against the patient's chest. This has the effect of enabling the pump to grip the sternum and pull it up to assist in the expansion of the chest cavity during the CPR technique.

Having described our invention what we claim is:

1. A cardiopulmonary resuscitating pump for pumping gas into and waste out of a patient, comprising:

a portable housing having a top wall adapted to be hand held in use, a bottom wall having a substantially planar undersurface adapted to rest on the chest of a patient, and a first side wall structure extending therebetween, said first side wall structure configured for successively moving between a contracted position and an expanded position in response to the application and release of external pressure applied manually to said top wall, application of external pressure to said top wall while said side wall is in said contracted position being transmitted to the patient via the bottom wall to effect simultaneous cardiac massage and ventilation;

a gas chamber defined within said walls and having a gas inlet and a gas outlet;

a waste chamber defined within said walls and having a waste inlet and a waste outlet;

an oropharyngeal airway in fluid connection with said gas outlet and said waste inlet;

valve means within said housing for permitting flow in only one direction through each of said gas inlet, said gas outlet, said waste inlet, and said waste outlet;

said valve means directing, during each movement of said first side wall structure to said contracted position, gas flow from said gas chamber into said oropharyngeal airway via said gas outlet and waste flow from said waste chamber via said waste outlet;

said valve means directing, during each movement of said first side wall structure to said expanded position, gas flow into said gas chamber via said gas inlet and waste flow from the patient into the waste chamber from said oropharyngeal airway via said waste inlet; and an additional valve means in said waste inlet to ensure that said waste inlet is closed during each movement of said first side wall structure to said contracted position.

2. A pump according to claim 1, wherein said housing includes a second side wall structure configured for successively moving between a contracted position and an expanded position simultaneous to said first side wall structure, said second side wall structure disposed between said top wall and bottom wall radially inwardly of, and coaxial with, said first side wall structure, one of said gas chamber and waste chamber being defined between said first and second side wall structures and the other of said chambers being defined within said second side wall structure.

3. A pump according to claim 1, wherein said first side wall structure comprises first and second sections, said first section being spaced from said second section via an interface block having upper and lower surfaces, said gas chamber being defined between said top wall, said upper surface and said first section, and said waste chamber being defined between said second section, said lower surface and said bottom wall, said gas and said waste inlets and outlets being positioned within said interface block.

4. A pump according to claim 3, wherein said second section of said first wall structure and said bottom wall form an inverted dome of resilient flexible material being air tightly secured to said lower surface of said interface block.

5. A pump according to claim 3, wherein said waste chamber contains a biasing spring to assist in expanding the volume of said waste chamber upon release of externally applied pressure.

6. A pump according to claim 5, wherein said gas chamber contains a biasing spring to assist in expanding said first side wall structure, and therefore the volume of said gas chamber, upon release of externally applied pressure.

7. A pump according to claim 6, wherein the spring force of said biasing spring in said waste chamber is less than the spring force of the biasing spring in said gas chamber to allow said waste chamber to contract before said gas chamber upon application of externally applied pressure.

8. A pump according to claim 1, wherein said gas and said waste outlets and inlets, extend through said bottom wall to communicate with the respective one of said gas and waste chambers.

9. A pump according to claim 1, wherein said valve means includes check valves disposed in said gas and said waste inlets and outlets to prevent reverse flow therethrough.

10. A pump according to claim 1, wherein said oropharyngeal airway includes a first passage in fluid connection with said gas outlet and a second passage in fluid connection with said waste inlet.

11. A pump according to claim 1, wherein said additional valve means comprises a valve member displaceable to engage a valve seat formed in said waste inlet and wherein said valve member seats against said valve seat during each movement of said first side wall structure to said contracted position and said valve member moves away from said valve seat during movement of said first side wall structure to said expanded position.

12. A pump according to claim 1, wherein said waste inlet has a bypass valve means that operates so that when in the open position gas entering the waste inlet is vented to atmosphere and when in the closed position gas entering the waste inlet passes to the waste chamber.

13. A pump according to claim 12, wherein the bypass valve includes externally operable means to actuate the valve from the closed to the open position.

14. A pump according to claim 13, wherein the bypass valve is in the open position when said first side wall structure is in said contracted position, said bypass valve means being in the closed position when said first side wall structure is in said expanded position.

15. A pump according to claim 1, wherein a suction cup is positioned on the bottom wall of the pump.

* * * * *